US012605872B2

(12) United States Patent
Kikuzawa

(10) Patent No.: US 12,605,872 B2
(45) Date of Patent: Apr. 21, 2026

(54) MULTI-LUMEN TUBE EXTRUSION MOLDING APPARATUS

(71) Applicant: PLA GIKEN CO., LTD., Osaka (JP)

(72) Inventor: Yoshiharu Kikuzawa, Osaka (JP)

(73) Assignee: PLA GIKEN CO., LTD., Osaka (JP)

( * ) Notice: Subject to any disclaimer, the term of this patent is extended or adjusted under 35 U.S.C. 154(b) by 309 days.

(21) Appl. No.: 18/418,247

(22) Filed: Jan. 20, 2024

(65) Prior Publication Data

US 2024/0253286 A1     Aug. 1, 2024

(30) Foreign Application Priority Data

Jan. 26, 2023   (JP) ................................. 2023-010355
Nov. 27, 2023   (JP) ................................. 2023-200245

(51) Int. Cl.
*B29C 48/11*        (2019.01)
*A61M 25/00*        (2006.01)
(Continued)

(52) U.S. Cl.
CPC ............. *B29C 48/11* (2019.02); *A61M 25/00* (2013.01); *B29C 48/0015* (2019.02); *B29C 48/002* (2019.02); *B29C 48/09* (2019.02); *B29C 48/1472* (2019.02); *B29C 48/1474* (2019.02); *B29C 48/255* (2019.02); *B29C 48/2566* (2019.02); *B29C 48/25686* (2019.02); *B29C 48/285* (2019.02); *B29C 48/303* (2019.02); *B29C 48/304* (2019.02); *B29C 48/32* (2019.02); *B29C 49/0021* (2013.01);
(Continued)

(58) Field of Classification Search
CPC .... B29C 48/11; B29C 48/303; B29C 49/0021
See application file for complete search history.

(56) References Cited

U.S. PATENT DOCUMENTS 4,078,454 A * 3/1978 Murakami ............ B29C 48/252
366/100
4,167,383 A * 9/1979 Murakami .............. B29C 48/49
425/133.1
(Continued)

FOREIGN PATENT DOCUMENTS

JP          6771313 B       10/2020
WO      2019/177018 A1     9/2019
WO      2020/262480 A1    12/2020

*Primary Examiner* — Benjamin A Schiffman
(74) *Attorney, Agent, or Firm* — Renner, Otto, Boisselle & Sklar, LLP

(57) ABSTRACT

Provided is an extrusion molding apparatus capable of producing a multi tube with which an outer shape of a cross section is close to a perfect circle. The multi-lumen tube extrusion molding apparatus includes a resin supplying portion, a die that has an extrusion port at a lower end portion and molds the multi-lumen tube as the resin supplied from the resin supplying portion is extruded vertically downward, and an outer surface molding apparatus that molds an outer surface of the extruded tube. In a state in which the resin is supplied from the resin supplying portion to the die, the outer surface molding apparatus depressurizes a molding space of circular cylindrical shape in a state in which the extruded tube is contained in the molding space to mold an outer surface of the contained multi-lumen tube to a circular cylindrical shape.

18 Claims, 6 Drawing Sheets

(51) Int. Cl.

| | | |
|---|---|---|
| *B29C 48/00* | (2019.01) | |
| *B29C 48/09* | (2019.01) | |
| *B29C 48/14* | (2019.01) | |
| *B29C 48/25* | (2019.01) | |
| *B29C 48/255* | (2019.01) | |
| *B29C 48/285* | (2019.01) | |
| *B29C 48/30* | (2019.01) | |
| *B29C 48/32* | (2019.01) | |
| *B29C 49/00* | (2006.01) | |
| B29L 23/00 | (2006.01) | |
| B29L 24/00 | (2006.01) | |
| B29L 31/00 | (2006.01) | |

(52) U.S. Cl.
CPC ..... *B29L 2023/007* (2013.01); *B29L 2023/22* (2013.01); *B29L 2024/006* (2013.01); *B29L 2031/7542* (2013.01)

(56) References Cited

U.S. PATENT DOCUMENTS

| | | | | |
|---|---|---|---|---|
| 4,185,954 A * | 1/1980 | Murakami | .............. | B29C 48/09 425/467 |
| 7,264,764 B2 * | 9/2007 | Miura | ..................... | B29C 48/13 264/150 |
| 8,178,034 B2 * | 5/2012 | Hegler | .................... | B29C 48/92 264/514 |
| 11,597,132 B2 * | 3/2023 | Kikuzawa | .............. | B29C 48/09 |
| 12,138,844 B2 * | 11/2024 | Kikuzawa | .............. | B29B 7/603 |
| 2019/0351600 A1 | 11/2019 | Kikuzawa | | |
| 2021/0362393 A1 | 11/2021 | Kikuzawa | | |

* cited by examiner

FIG. 8A
FIG. 8B
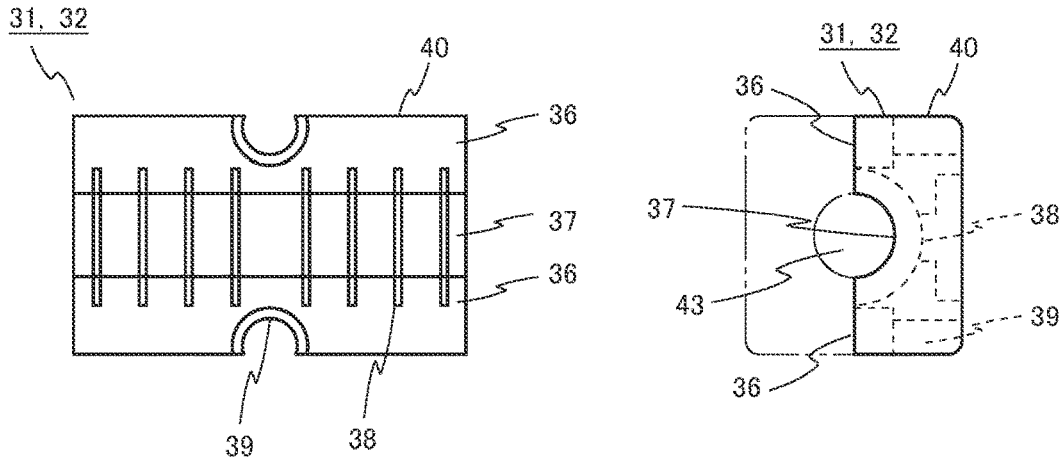
FIG. 9A
FIG. 9B
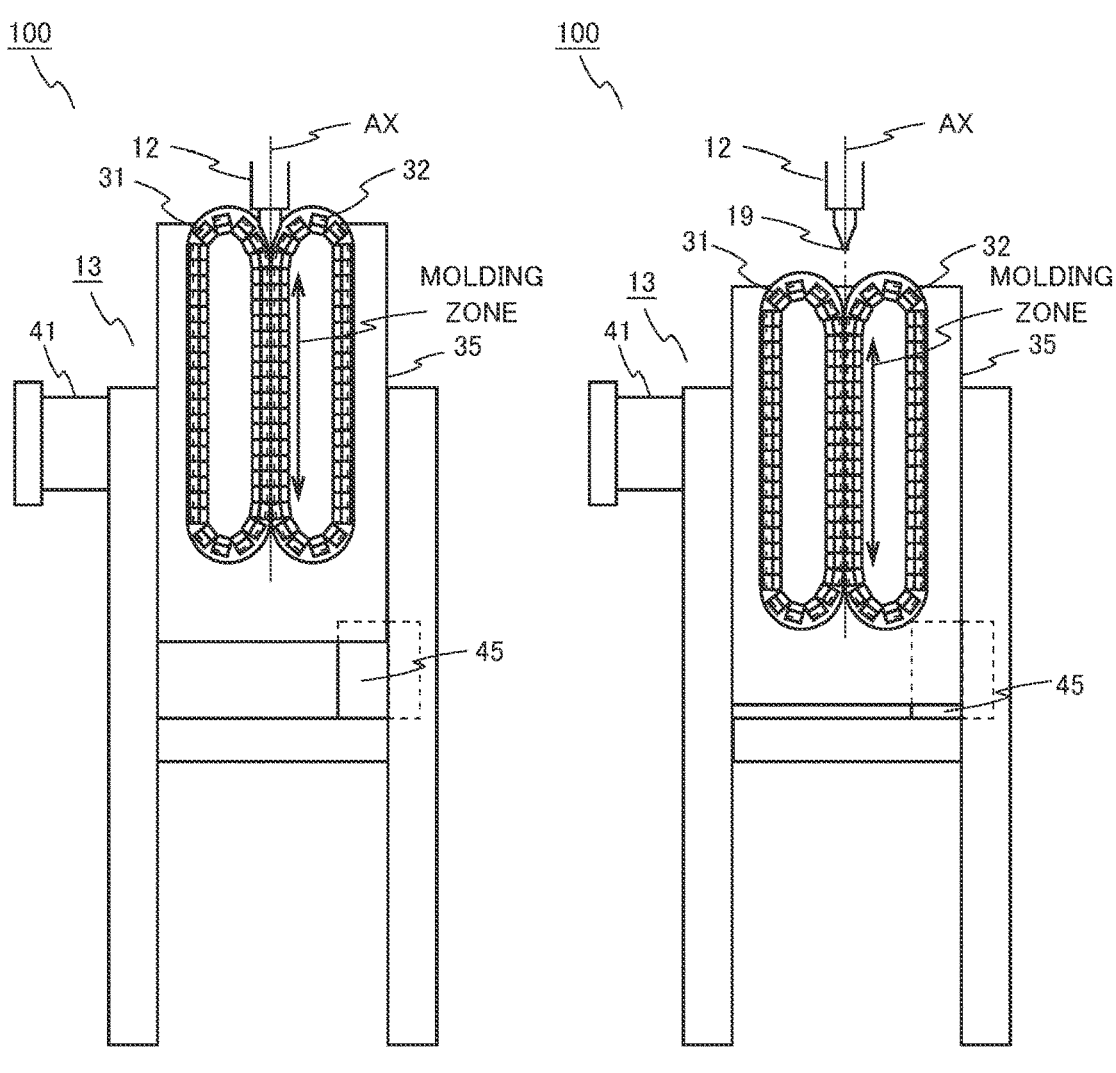

MULTI-LUMEN TUBE EXTRUSION MOLDING APPARATUS

CROSS REFERENCE TO RELATED APPLICATION

The disclosures of Japanese Patent Application No. 2023-010355 filed on Jan. 26, 2023 and Japanese Patent Application No. 2023-200245 filed on Nov. 27, 2023 are incorporated in this description by reference.

BACKGROUND OF THE INVENTION

Field of the Invention

The present invention relates to an extrusion molding apparatus for a multi-lumen tube having two or more conduits.

Description of the Background Art

A multi-lumen tube having a plurality of conduits (lumens) is used, for example, in medical applications such as catheter surgery, endoscopic surgery, etc. The plurality of conduits of the multi-lumen tube are used for electrode positioning, guide wire insertion, balloon inflation, drug solution injection, suction of a body fluid or a blood clot, etc. By using the multi-lumen tube, it is made possible to use and manipulate a plurality of devices with a single tube. For example, an extrusion molding apparatus capable of thickening a resin layer that separates a flow passage and a flow passage from each other without increasing a thickness of a resin layer between an outer shape surface of the tube and the flow passages is described in Japanese Patent Publication No. 6771313.

SUMMARY OF THE INVENTION

A multi-lumen tube extrusion molding apparatus such as described in Japanese Patent Publication No. 6771313 includes conduit forming members of tubular shape and can form a plurality of conduits by extruding resin while injecting air from the conduit forming members. However, when extrusion molding is performed while injecting air from the conduit forming members, an uncured tube immediately after extrusion molding deforms due to pressure of the injected air and it is difficult to make an outer shape of the tube a perfect circle. A tube of an outer shape that is not a perfect circle is not suited for medical applications where insertion into a body is performed and a multi-lumen tube with which an outer shape of a cross section is close to a perfect circle is being demanded. There is also a problem in that when attempts are made to make the outer shape of the tube smaller or increase the number of conduits provided in the tube, a thickness of a resin portion from an outer circumferential surface of the tube to a conduit formed close to the outer circumferential surface becomes thin such that the resin portion breaks easily and a yield decreases.

An object of the present invention is thus to provide an extrusion molding apparatus capable of producing a multi-lumen tube with which an outer shape of a cross section is close to a perfect circle.

In order to solve the above problem, an extrusion molding apparatus according to the present invention is that for extrusion molding a multi-lumen tube having two or more conduits and includes a resin supplying portion that extrudes a molten resin, a die that has an extrusion port at a lower end portion and molds the multi-lumen tube as the resin supplied from the resin supplying portion is extruded vertically downward, an outer surface molding apparatus that molds an outer surface of the multi-lumen tube extruded from the die, a gas supplying apparatus, and a depressurizing apparatus. The die includes an inner die, two or more conduit molding members of tubular shapes that are provided in correspondence with the respective conduits of the multi-lumen tube and with each of which a front end portion projects from a lower end portion of the inner die and a remaining portion is positioned in an interior of the inner die and each having a penetrating hole and having, at the front end portion, a portion of outer shape corresponding to a cross-sectional shape of the corresponding conduit, and an outer die of tubular shape that surrounds the inner die and the portions projecting from the lower end portion of the inner die and forms a resin flow passage between its inner surface and an outer surface of the inner die. The outer surface molding apparatus includes a plurality of first mold blocks each having a flat surface with which an outer shape is a rectangular shape, a groove of rectilinear shape that is provided on the flat surface and with which a cross section in a direction orthogonal to the flat surface is a semicircular shape, and a slit or a pore that penetrates through the groove, second mold blocks of the same shape and same number as the first mold blocks, and a driving mechanism that pairs and circulates the first mold blocks and the second mold blocks. The driving mechanism causes, in a molding zone provided vertically below the die, the flat surfaces of each paired first mold block and second mold block to be in surface contact with each other such that the grooves thereof overlap mutually, a molding space with which a lateral cross section is of a perfect circular shape and a center of the lateral cross section coincides substantially with a central axis of the die to be formed between the mutually overlapped grooves, and a successive plurality of pairs of the first mold block and the second mold block to undergo rectilinear movement vertically downward along the central axis of the die and causes, outside the molding zone, each paired first mold block and second mold block to separate from each other. In a state in which the resin is supplied from the resin supplying portion to the die, a gas is supplied from the gas supplying apparatus to each of the conduit molding members, the supplied gas is injected from front ends of the penetrating holes, the driving mechanism causes, in a state in which the multi-lumen tube extruded from the die is contained in the molding space of each of the successive plurality of pairs of the first mold block and the second mold block, the first mold blocks and the second mold blocks to move vertically downward in accordance with the extrusion of the multi-lumen tube, and the molding space is depressurized by the depressurizing apparatus to put the outer surface of the multi-lumen tube contained in the molding space in close contact with inner surfaces of the grooves.

As another mode, the outer surface molding apparatus may include a first belt formed of a material with flexibility and having a flat surface, a groove of rectilinear shape that is provided on the flat surface and with which a cross section in a direction orthogonal to the flat surface is a semicircular shape, and a slit or a pore that penetrates through the groove, a second bell formed of the same material as the first belt and having the same shape as the first belt, and a driving mechanism that circulates the first belt and the second belt. In this case, the driving mechanism causes, in a molding zone provided vertically below the die, the flat surfaces of the first belt and second belt to be in surface contact with each other such that the grooves thereof overlap mutually, a molding space with which a lateral cross section is of a perfect circular shape and a center of the lateral cross section coincides substantially with a central axis of the die to be formed between the mutually overlapped grooves, and the first belt and the second belt to undergo rectilinear movement vertically downward along the central axis of the die and causes, outside the molding zone, the first belt and the second belt to separate from each other. In a state in which the resin is supplied from the resin supplying portion to the die, a gas is supplied from the gas supplying apparatus to each of the conduit molding members, the supplied gas is injected from front ends of the penetrating holes, the driving mechanism causes, in a state in which the multi-lumen tube extruded from the die is contained in the molding space formed by the first belt and the second belt, the first belt and the second belt to move vertically downward in accordance with the extrusion of the multi-lumen tube, and the molding space is depressurized by the depressurizing apparatus to put the outer surface of the multi-lumen tube contained in the molding space in close contact with inner surfaces of the grooves.

By the present invention, an extrusion molding apparatus capable of producing a multi-lumen tube with which an outer shape of a cross section is close to a perfect circle can be provided.

The aforementioned and other objects, features, aspects, and effects of the present invention will be made clearer by the following detailed description made with reference to the accompanying drawings.

BRIEF DESCRIPTION OF THE DRAWINGS

FIG. 8A is a plan view of a mold block shown in FIG. 3;

FIG. 8B is a right side view of the mold block shown in FIG. 8A;

FIG. 9A is an enlarged view of an outer surface molding apparatus shown in FIG. 1;

FIG. 9B is an enlarged view of the outer surface molding apparatus shown in FIG. 1;

DESCRIPTION OF THE PREFERRED EMBODIMENTS

First Embodiment

Figure 1:
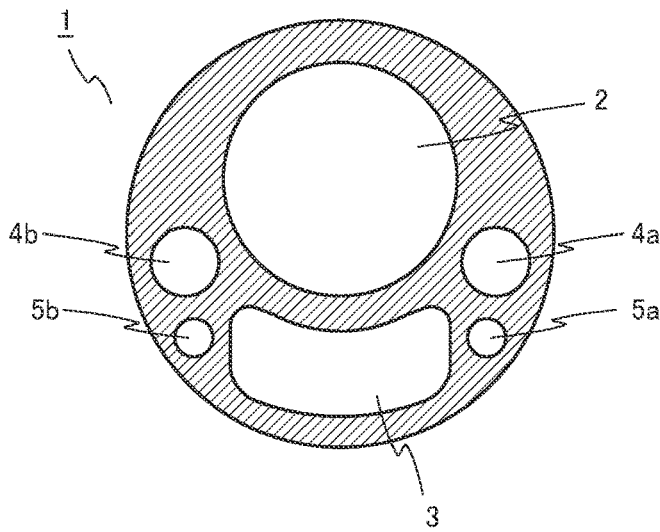
FIG. 1 is a sectional view showing an example of a multi-lumen tube according to a first embodiment.

FIG. 1 is a sectional view showing an example of a multi-lumen tube according to a first embodiment.

A multi-lumen tube 1 is a tube made of resin that is used in medical applications such as catheter surgery, endoscopic surgery, etc., and has a plurality of conduits (lumens) 2 to 5b that extend in a length direction of the tube. The conduits 2 to 5b are used for insertion of various instruments such as a guide wire, balloon, signal line, etc., injection of a drug solution, suction of a body fluid, etc. Cross-sectional shapes of the conduits 2 to 5b are not restricted in particular and may be circular as in conduits 2, 4a, 4b, 5a, and 5b or may be an irregular shape as in conduit 3. Also, sizes (inner diameters) of the conduits 2 to 5b can be set as appropriate according to application. The number and positions of the conduits are also not restricted in particular. A material of the multi-lumen tube 1 is not restricted in particular and polyethylene, polypropylene, polyamide, polyurethane, polyether, polyester, polyimide, fluororesin, silicone rubber, etc., can be cited. An outer shape of a lateral cross section of the multi-lumen tube 1 is a perfect circle and, in a case of a tube for a medical application, a diameter is, for example, not more than 10 mm.

Figure 2:
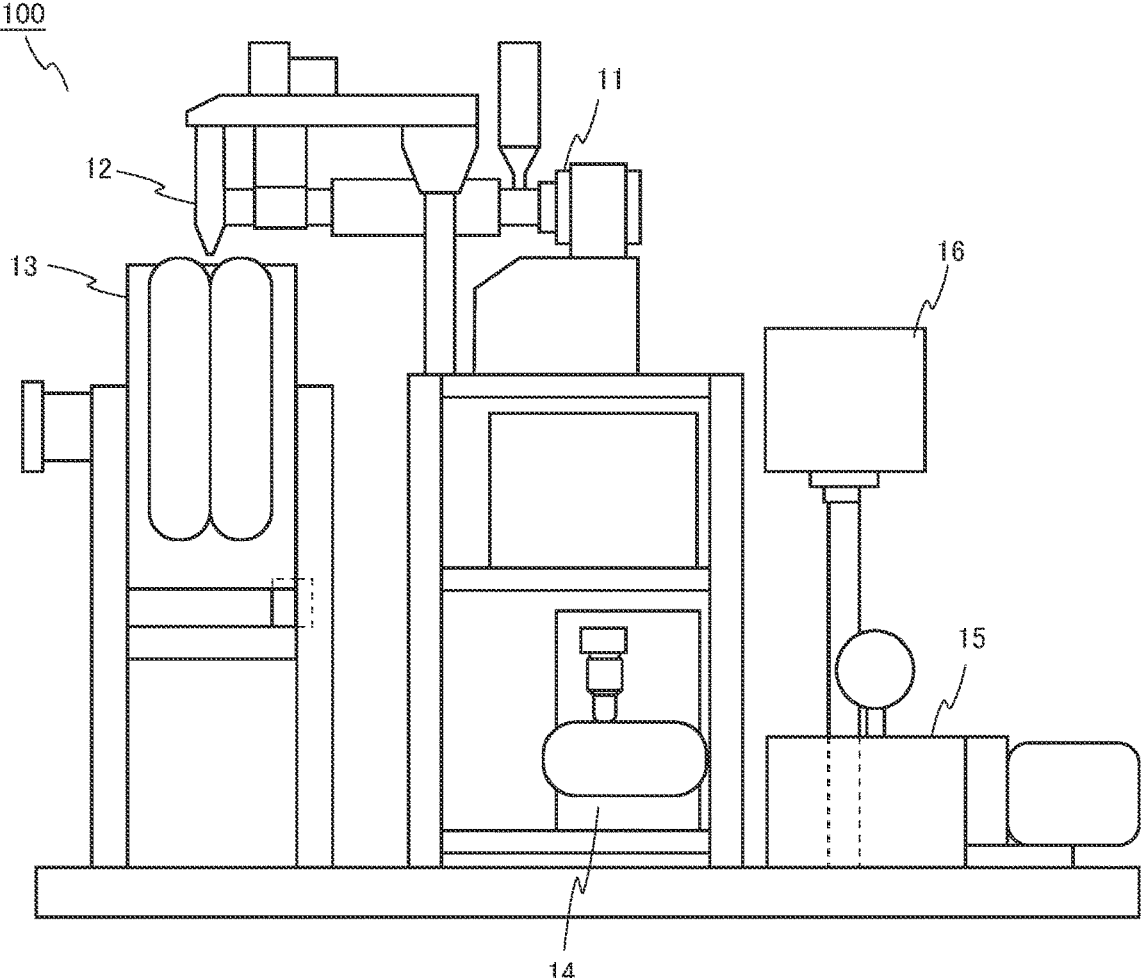
FIG. 2 is a diagram showing the general arrangement of a multi-lumen tube extrusion production apparatus according to the first embodiment.

FIG. 2 is a diagram showing the general arrangement of a multi-lumen tube extrusion production apparatus according to the first embodiment.

An extrusion molding apparatus 100 is an apparatus for extrusion molding the multi-lumen tube 1 using a resin and includes an extruder 11, a die 12, an outer surface molding apparatus 13, a gas supplying apparatus 14, a depressurizing apparatus 15, and a controller 16. The respective constituent units of the extrusion molding apparatus 100 are fixed on a predetermined table, etc. Also, although unillustrated, a cooling apparatus that cools the extrusion molded multi-lumen tube 1, a drawing apparatus that draws out the multi-lumen tube 1, etc., are provided as appropriate at a downstream side of the die 12.

The extruder 11 is, for example, a screw extruder and can melt pellets of the resin and perform extrusion at a fixed speed from a discharge port at a front end. A gear pump for adjusting a flow rate of the resin may be provided between the extruder 11 and the die 12.

Figure 3:
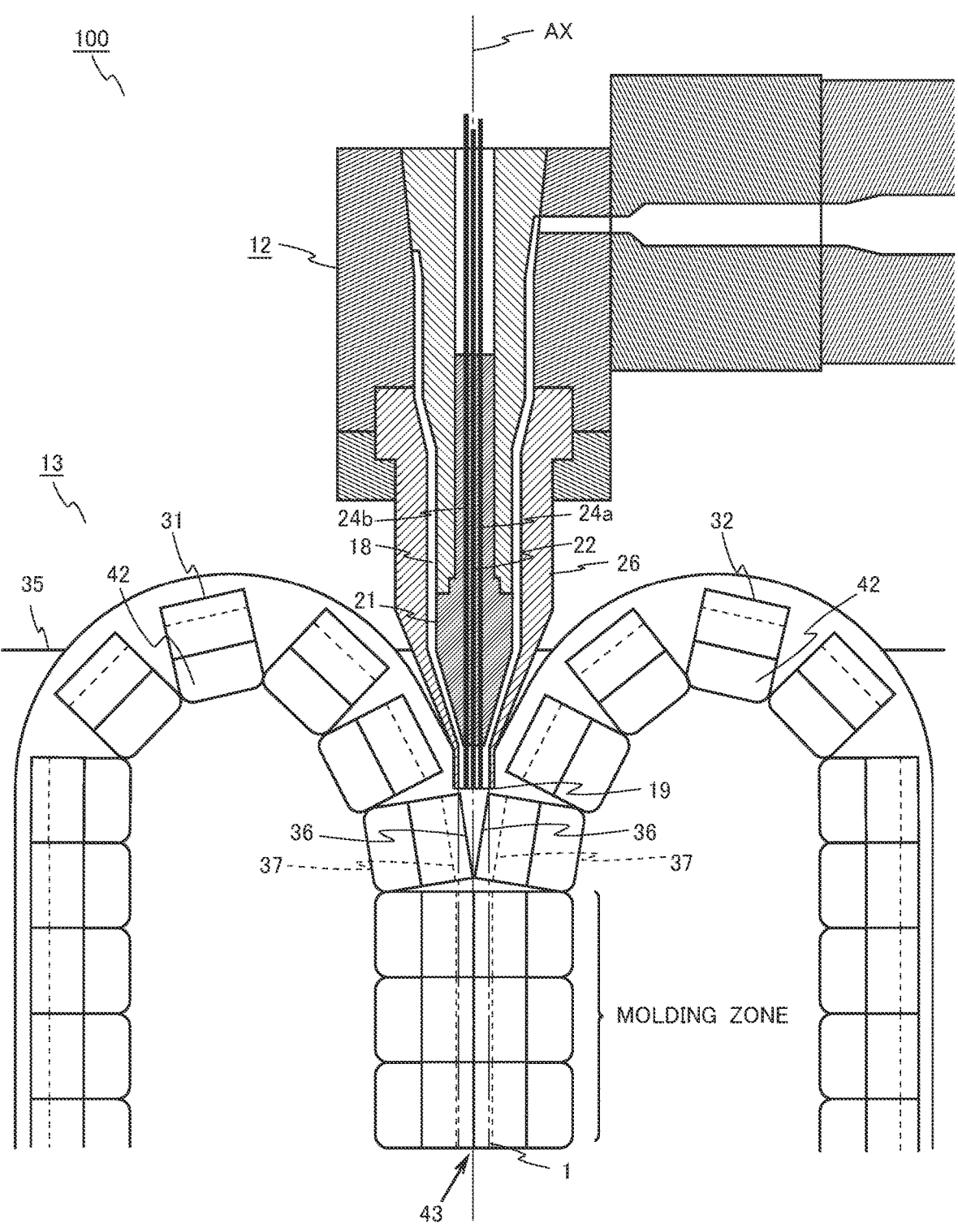
FIG. 3 is a longitudinal sectional view of a die shown in FIG. 1.
Figure 4:
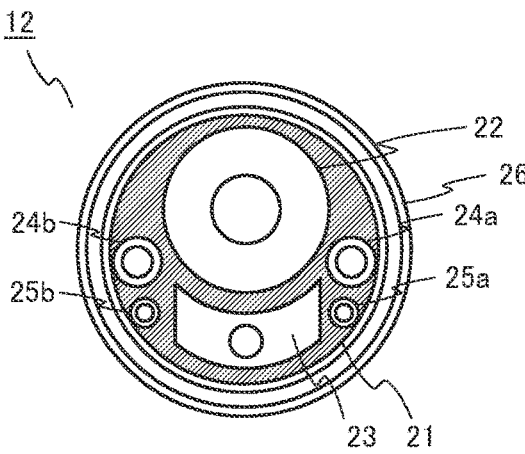
FIG. 4 is an end view of an extrusion port of the die shown in FIG. 1.
Figure 5:
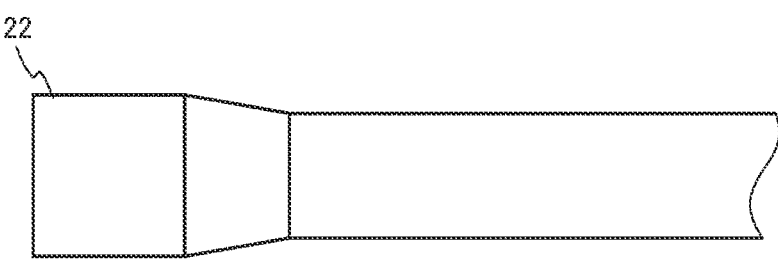
FIG. 5 is a diagram showing a conduit molding member shown in FIG. 4.
Figure 6A:
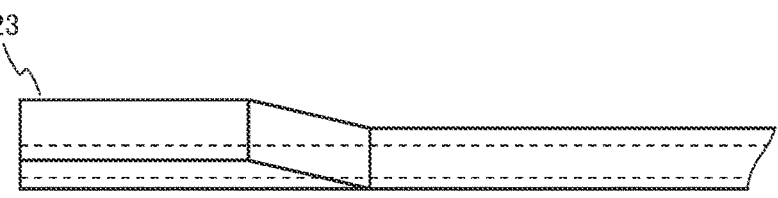
FIG. 6A is a right side view of the conduit molding member shown in FIG. 4.
Figure 6B:
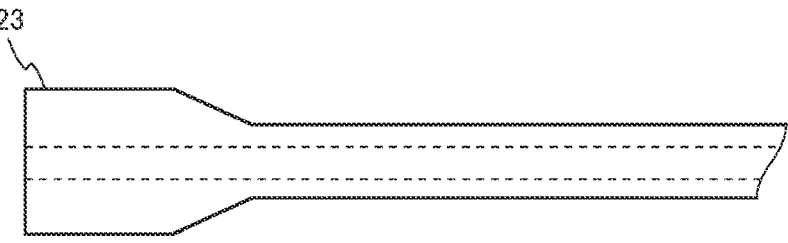
FIG. 6B is a bottom view of the conduit molding member shown in FIG. 6A.
Figure 7:
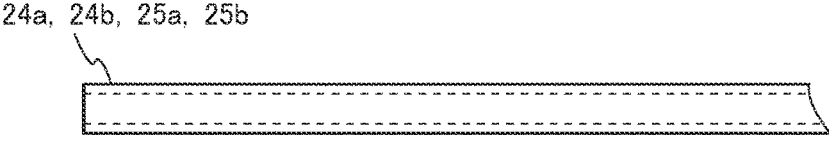
FIG. 7 is a diagram showing the conduit molding member shown in FIG. 4.

FIG. 3 is a longitudinal sectional view of the die shown in FIG. 1, FIG. 4 is an end view of an extrusion port of the die shown in FIG. 1, and FIG. 5 to FIG. 7 are diagrams showing conduit molding members shown in FIG. 4. In more detail, FIG. 5 corresponds to being a right side view of a conduit molding member 22 shown in FIG. 4, FIG. 6A corresponds to being a right side view of a conduit molding member 23 shown in FIG. 4, FIG. 6B corresponds to being a bottom view of the conduit molding member 23 shown in FIG. 6A, and FIG. 7 corresponds to being a right side view of any of conduit molding members 24a, 24b, 25a, and 25b shown in FIG. 4.

The die 12 has a resin flow passage 18 through which the resin extruded from the extruder 11 is made to flow and an extrusion port 19 at a lower end portion and molds the multi-lumen tube 1 as the resin supplied from the extruder 11 is extruded vertically downward. The die 12 includes an inner die 21, the plurality of conduit molding members 22 to 25b, portions of which are positioned in an interior of the inner die 21, and an outer die 26 of tubular shape. Here, although in the present embodiment, the inner die 21 is constituted of two members, the structure of the inner die 21 is not restricted in particular as long as the conduit molding members 22 to 25b can be held and the resin flow passage 18 can be formed with the outer die 26.

The conduit molding members 22 to 25b are all members of tubular shape each having a penetrating hole for injecting a gas. The conduit molding members 22, 23, 24a, 24b, 25a, and 25*b* are provided in correspondence to the conduits 2, 3, 4*a*, 4*b*, 5*a*, and 5*b*, respectively, of the multi-lumen tube 1. As shown in FIG. 4 to FIG. 7, the conduit molding members 22, 23, 24*a*, 24*b*, 25*a*, and 25*b* have, at front end portions, portions of outer shape corresponding to respective cross-sectional shapes of the conduits 2, 3, 4*a*, 4*b*, 5*a*, and 5*b* of the multi-lumen tube 1. The front end portions of the conduit molding member 22 to 25*b* project from a lower end of the inner die 21 and remaining portions of the conduit molding members 22 to 25*b* are contained in an interior of the inner die 21. The conduit molding members 22 to 25*b* are fixed to the inner die 21 via an unillustrated member. The gas supplying apparatus 14 is connected to the conduit molding members 22 to 25*b* via unillustrated tubes, etc., and a gas such as air, etc., is supplied from the gas supplying apparatus 14 during extrusion molding of the multi-lumen tube 1.

As shown in FIG. 3, the conduit molding members 22, 24*a*, and 24*b* differ in length. Although just the three conduit molding members 22, 24*a*, and 24*b* are shown in FIG. 3 for the sake of illustration, the conduit molding members 22 to 25*b* all differ in length and are mutually shifted in respective upper end positions. By differing the upper end positions of the conduit molding members 22 to 25*b*, it is made easy to identify the conduit molding members 22 to 25*b* and production and maintenance of the apparatus can be facilitated.

Here, with the present embodiment, each of the conduit molding members 22 to 25*b* is formed as a single member, at least one of the conduit molding members 22 to 25*b* may be arranged from a first member of tubular shape of a predetermined length that includes the front end portion and a second member of tubular shape with which a lower end portion is detachably connected to the first member. Outer shapes and sizes of the front end portions of the conduit molding members 22 to 25*b* differ in accordance with a shape (specifications) of the multi-lumen tube 1 to be molded and by arranging such that the front end portions are separable, it is made possible to mold the multi-lumen tubes 1 of different shapes by exchange of the front end portions.

The outer die 26 is a member of tubular shape that surrounds the inner die 21 and portions of the conduit molding members 22 to 25*b* that project from a lower end portion of the inner die 21. An inner diameter of the outer die 26 is greater than an outer shape of the inner die 21. The resin flow passage 18 that is constituted of a predetermined gap is thereby formed between an outer surface of the inner die 21 and an inner circumferential surface of the outer die 26.

Details of the outer surface molding apparatus 13 will now be described with reference to FIG. 2, FIG. 3, FIG. 8, and FIG. 9.

FIGS. 8A and 8B shows diagrams of a mold block shown in FIG. 3 and FIG. 9 shows enlarged views of the outer surface molding apparatus shown in FIG. 1. In more detail, FIG. 8A is a plan view of the mold block shown in FIG. 3 and FIG. 8B is a right side view of the mold block shown in FIG. 8A. A first mold block 31 and a second mold block 32 are of the same shape and thus in the description of FIGS. 8A and 8B, the two are not distinguished and are referred to simply as "mold block."

The outer surface molding apparatus 13 is an apparatus that molds an outer surface of the multi-lumen tube 1, extruded from the die 12, to a perfect circular shape. The outer surface molding apparatus 13 includes a plurality of the first mold blocks 31, the same number of the second mold blocks 32 as the first mold blocks 31, and a driving mechanism 35 that circulates the first mold blocks 31 and the second mold blocks 32.

As shown in FIGS. 8A and 8B, the mold blocks 31 and 32 each have a block portion 40 that has a flat surface 36 having an outer shape that is substantially rectangular and a groove 37 of rectilinear shape that is provided on the flat surface 36, and a plurality of slits 38 that are provided on the block portion 40. The groove 37 provided on the block portion 40 is a portion for molding the outer surface of the multi-lumen tube 1 to the perfect circular shape and a cross-sectional shape of the groove 37 in a direction orthogonal to its extension direction and the flat surface 36 is a uniform semicircular shape. That is, the groove 37 has a semicircular columnar shape. Each of the slits 38 extends in a direction of crossing the groove 37 (direction orthogonal to the extension direction of the groove 37) and penetrates through the block portion 40 from the flat surface 36 to a surface at a rear surface side of the flat surface 36. The slits 38 are used for depressurizing an interior of the groove 37 by the depressurizing apparatus 15 during extrusion molding. The block portion 40 is also provided with recesses 39 that are used to fix each of the mold blocks 31 and 32 to a mold block base 42 (see FIG. 3) of the driving mechanism 35. Here, pores that penetrate through the block portion 40 in the direction orthogonal to the flat surface 36 may be provided in place of the slits 38 or together with the slits 38.

The driving mechanism 35 includes a motor 41 and, by a rotating force of the motor 41, pairs and circulates the first mold blocks 31 and the second mold blocks 32 along loci of track shapes. As shown in FIG. 2 and FIG. 9, the driving mechanism 35 causes the flat surfaces 36 of the separated first mold blocks 31 and second mold blocks 32 to be in surface contact with each other vertically below the die 12 in accompaniment with the circulation of the first mold blocks 31 and second mold blocks 32. In this process, entireties of the respective flat surfaces 36 of each paired first mold block 31 and second mold block 32 contact mutually such that the respective grooves 37 of the first mold block 31 and the second mold block 32 overlap completely and a molding space 43 of circular columnar shape with a lateral cross section of perfect circular shape is formed between the overlapped grooves 37 (see FIG. 8B). A center of the lateral cross section of the molding space 43 coincides substantially with the central axis of the die 12. In a state in which the molding space 43 of circular columnar shape is formed between the paired first mold block 31 and second mold block 32, the driving mechanism 35 moves the first mold block 31 and the second mold block 32 vertically downward along the central axis of the die 12. In this process, by moving the first mold blocks 31 and the second mold blocks 32 such that a successive plurality of pairs of first mold blocks 31 and second mold blocks 32 become linked without any gaps, a state is reached where the molding spaces 43 formed by the plurality of pairs of first mold blocks 31 and second mold blocks 32 are made continuous. Here, a portion where the first mold blocks 31 and the second mold blocks 32 move vertically downward along the central axis of the die 12 with the flat surfaces 36 thereof being put in surface contact with each other will be referred to as a "molding zone." Thereafter, the paired first mold blocks 31 and second mold blocks 32 separate again and circulate along the loci of track shapes.

As shown in FIGS. 9A and 9B, the outer surface molding apparatus 13 according to the present embodiment is further provided with an elevating/lowering mechanism 45.

The elevating/lowering mechanism 45 includes a motor or an air cylinder, etc., and, as shown in FIG. 9A and FIG. 9B, is capable of moving the outer surface molding apparatus 13 in a vertical direction (up/down direction). By changing a vertical position of the outer surface molding apparatus by the elevating/lowering mechanism 45, a vertical distance from the extrusion port 19 of the die 12 to the molding zone in the outer surface molding apparatus 13 can be changed.

With the extrusion molding apparatus 100 according to the present embodiment, an outer diameter of the multi-lumen tube 1 to be molded is determined by a radius of the grooves 37 formed on the first mold blocks 31 and the second mold blocks 32. With a general extrusion molding apparatus, a die having an extrusion port of an inner diameter equal to an outer diameter of a tube to be molded is used and dies must be prepared according to each outer diameter of tubes to be molded. With the present embodiment, by moving the outer surface molding apparatus 13 downward by the elevating/lowering mechanism 45 and extending a time from when the multi-lumen tube 1 is extruded from the die 12 until when it is inserted into the molding spaces 43 of the first mold blocks 31 and the second mold blocks 32, the multi-lumen tube 1 before curing can be drawn out by gravity and decreased in outer diameter. Therefore, with the extrusion molding apparatus 100 according to the present embodiment, the outer diameter of the multi-lumen tube 1 to be molded can be changed by exchanging the first mold blocks 31 and the second mold blocks 32 and changing the up/down position of the outer surface molding apparatus 13 and there is no need to prepare the die 12 for each outer diameter. A cost required to change a dimension of the multi-lumen tube 1 can thus be suppressed.

The gas supplying apparatus 14 is connected to respective upper end portions of the conduit molding members 22 to 25b of the die 12 via unillustrated tubes, etc., and supplies the gas to the penetrating holes of the conduit molding members 22 to 25b. The gas supplying apparatus 14 includes a pump, valve, a regulator for flow regulation, etc. Although the gas supplied by the gas supplying apparatus 14 is not restricted in particular, it is preferable to use air.

The depressurizing apparatus 15 is, for example, a vacuum pump and is connected to the outer surface molding apparatus 13 via an unillustrated tube or piping, etc. During extrusion molding, the depressurizing apparatus 15 draws vacuum from rear surfaces (surfaces at opposite sides to the flat surfaces 36) of the first mold blocks 31 and the second mold blocks 32 via the slits 38.

The controller 16 includes a computer that includes a CPU, a memory, a storage device, a communication interface, etc., and is connected to the extruder 11, the outer surface molding apparatus 13 (driving mechanism 35), the gas supplying apparatus 14, and the depressurizing apparatus 15 via unillustrated signal lines. The controller 16 controls operations of the respective apparatuses that are connected via the signal lines. Also, the controller 16 may also perform control of various apparatuses disposed at an upstream side and a downstream side of the extrusion molding apparatus 100.

A method for extrusion molding the multi-lumen tube 1 by the extrusion molding apparatus 100 will now be described with reference to FIG. 1 to FIG. 9B.

In a state in which the resin is supplied from the extruder 11 to the die 12, air is supplied from the gas supplying apparatus 14 to respective hollow portions (penetrating portions) of the conduit molding members 22 to 25b and air is injected from the front ends of the conduit molding members 22 to 25b. The conduits 2 to 5b of shapes corresponding to the outer shapes of the front end portions of the conduit molding members 22 to 25b are respectively formed in the multi-lumen tube 1 immediately after extrusion and by air being injected from the front ends of the conduit molding members 22 to 25b, the shapes of the formed conduits 2 to 5b can be maintained until the resin cures.

Next, the multi-lumen tube 1 extruded from the die 12 is inserted into the molding spaces 43 formed between the successive plurality of pairs of first mold blocks 31 and second mold blocks 32 inside the molding zone. In the state in which the extruded multi-lumen tube 1 is contained in the molding spaces 43, the driving mechanism 35 moves the first mold blocks 31 and the second mold blocks 32 vertically downward in accordance with the extrusion of the multi-lumen tube 1 (that is, at substantially the same speed as an extrusion speed of the multi-lumen tube 1).

The molding space 43 (molding portion) between at least one pair of the first mold block 31 and second mold block 32 in the molding zone is depressurized by the depressurizing apparatus 15. Therefore, the outer surface of the multi-lumen tube 1 contained in the molding space 43 is put in a state of being in close contact with (being suctioned to) inner surfaces of the grooves 37 that constitute the molding space 43. The first mold block 31 and the second mold block 32 are moved vertically downward with the outer surface of the multi-lumen tube 1 being put in close contact with entire inner surfaces of the grooves 37. The resin cures while the first mold block 31 and the second mold block 32 move vertically downward and the multi-lumen tube 1 with which the outer shape of the cross section is a perfect circle can be obtained.

As described above, by the extrusion molding apparatus 100 according to the present embodiment, since the outer surface molding apparatus 13 is used to mold the outer shape of the cross section of the multi-lumen tube 1 immediately after extrusion, a multi-lumen tube with which the outer shape of the cross section is close to a perfect circle can be produced. The extrusion molding apparatus 100 according to the present embodiment is especially favorable for production of tubes for medical applications with which it is required that the outer shape of the cross section be a perfect circle.

Also, with the extrusion molding apparatus 100 according to the present embodiment, the outer surface of the multi-lumen tube 1 that is soft immediately after extrusion is put in close contact with the inner surfaces of the grooves 37 of the first mold block 31 and the second mold block 32 by vacuum drawing. Thus, even when the number of conduits is increased or the tube is decreased in diameter, a resin portion between the outer surface of the tube and the conduits can be prevented from breaking due to pressure of the air injected from the conduit molding members 22 to 25b. The extrusion molding apparatus 100 according to the present embodiment is therefore especially suited for production of the multi-lumen tube 1 for medical applications with a small diameter of not more than 10 mm, not more than 8 mm, or not more than 5 mm.

Second Embodiment

Figure 10:
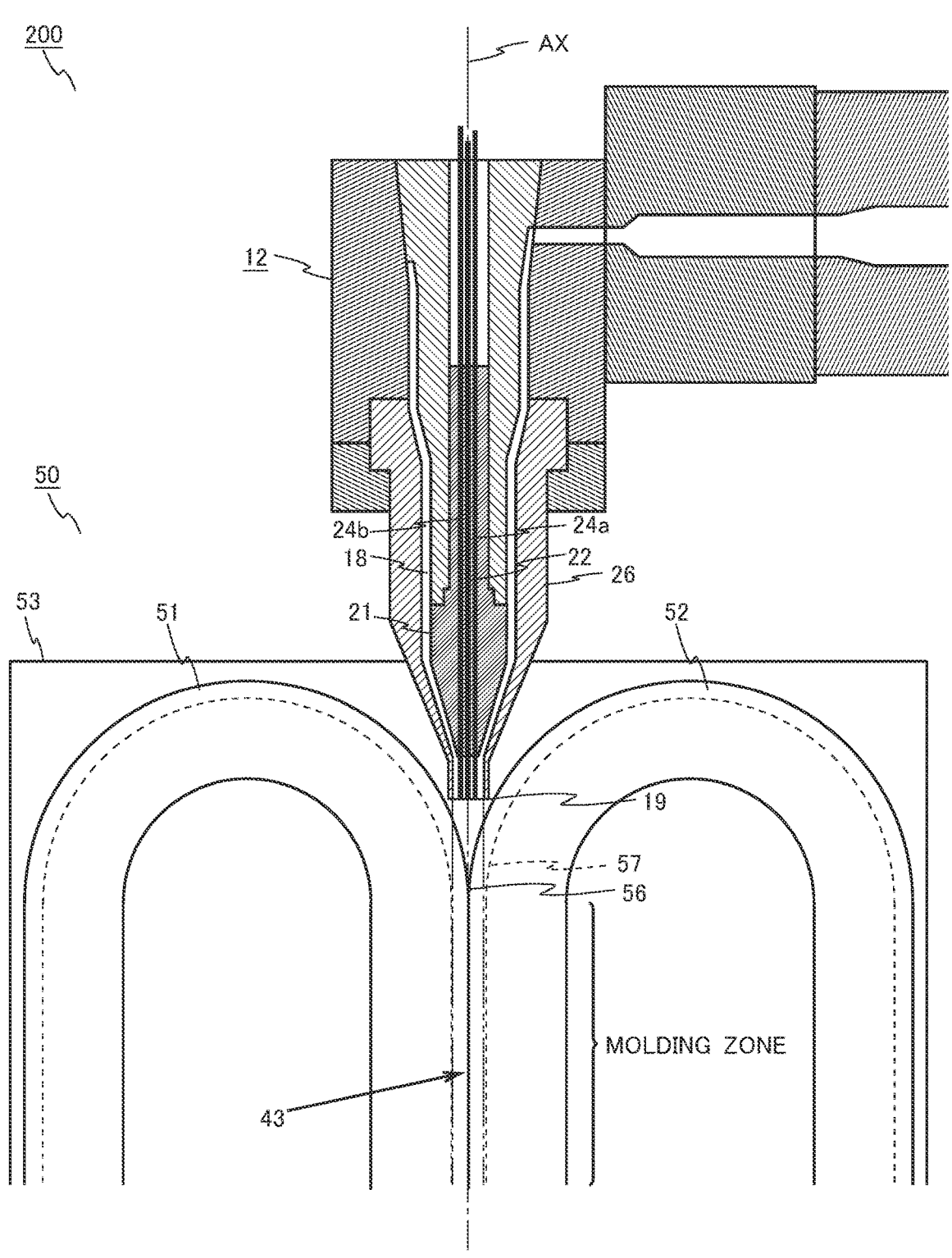
FIG. 10 is a sectional view showing an example of a multi-lumen tube according to a second embodiment.
Figure 11A:
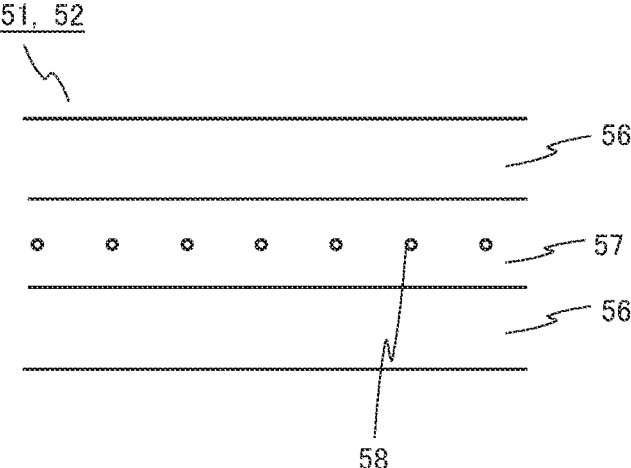
FIG. 11A is a plan view of a belt shown in FIG. 10.
Figure 11B:
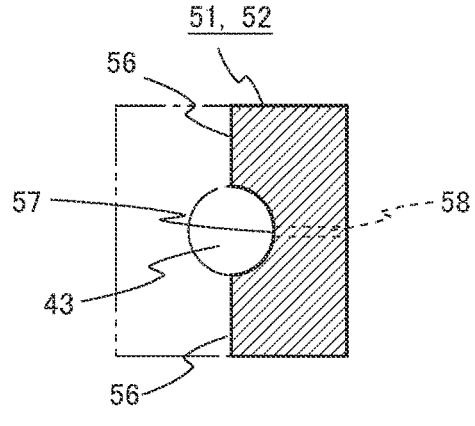
FIG. 11B is a sectional view of the belts shown in FIG. 10.

FIG. 10 is a sectional view showing an example of a multi-lumen tube according to a second embodiment and FIG. 11 shows diagrams showing a belt (belts) shown in FIG. 10. Points of difference between the present embodiment and the first embodiment will mainly be described below.

An extrusion molding apparatus 200 according to the present embodiment includes an outer surface molding apparatus 50 in place of the outer surface molding apparatus 13 according to the first embodiment. The outer surface molding apparatus 50 includes a first belt 51, a second belt 52, and a driving mechanism 53 that circulates the first belt 51 and the second belt 52.

The first belt 51 and the second belt 52 are members that are formed from a material with flexibility such as rubber, resin, silicone, etc. As shown in FIG. 11, the first belt 51 and the second belt 52 each have a flat surface 56, a groove 57 that is provided on the flat surface 56, and a plurality of pores 58 that penetrate through the groove 57. The groove 57 is a portion for molding the outer surface of the multi-lumen tube 1 to a perfect circular shape and a cross-sectional shape of the groove 57 in a direction orthogonal to its extension direction and the flat surface 56 is a uniform semicircular shape. That is, the groove 57 has a semicircular columnar shape when the first belt 51 and the second belt are stretched rectilinearly. The plurality of pores 58 are formed at predetermined intervals along an extension direction of the first belt 51 and the second belt 52. The pores 58 are used for depressurizing an interior of the groove 57 by the depressurizing apparatus 15 during extrusion molding. Here, slits that penetrate through the groove 57 extending in a direction orthogonal to the extension direction of the first belt 51 and the second belt 52 and the flat surface 56 may be provided in place of the pores 58 or together with the pores 58.

The first belt 51 and the second belt 52 may be gear belts. In this case, gears that engage with gears (not shown) of the driving mechanism 53 are formed at a fixed pitch at portions at opposite sides to the flat surfaces 56.

The driving mechanism 53 includes an unillustrated motor and, by a rotating force of the motor, circulates the first belt 51 and the second belt 52 along loci of track shapes. As shown in FIG. 10, the driving mechanism 53 causes the flat surfaces 56 of the separated first belt 51 and the second belt 52 to be in surface contact with each other vertically below the die 12 in accompaniment with the circulation of the first belt 51 and the second belt 52. In this process, the respective grooves 57 of the first belt 51 and the second belt 52 overlap completely and a molding space 43 of circular columnar shape with the lateral cross section of perfect circular shape is formed between the overlapped grooves 57. The center of the lateral cross section of the molding space 43 coincides substantially with the central axis of the die 12. The driving mechanism 35 circulates the first belt 51 and the second belt 52 while maintaining a state in which the molding space 43 of circular columnar shape is formed by the first belt 51 and the second belt 52 inside the molding zone. Outside the molding zone, the driving mechanism 53 separates the first belt 51 and the second belt 52 again.

During extrusion molding of the multi-lumen tube, the multi-lumen tube 1 extruded from the die 12 is inserted into the molding space 43 formed between the first belt 51 and the second belt 52. In the state in which the extruded multi-lumen tube 1 is contained in the molding spaces 43, the driving mechanism 53 circulates the first belt 51 and the second belt 52 in accordance with the extrusion of the multi-lumen tube 1 (that is, at substantially the same speed as the extrusion speed of the multi-lumen tube 1).

By the depressurizing apparatus 15, an interior of the molding space 43 is depressurized through the pores 58 penetrating through the first belt 51 and the second belt 52. The outer surface of the multi-lumen tube 1 before curing that is contained in the molding space 43 is put in a state of being in close contact with the inner surfaces of the grooves 57 of the first belt 51 and the second belt 52. The resin cures while the first belt 51 and the second belt 52 are circulated with the outer surface of the multi-lumen tube 1 being put in close contact with entire inner surfaces of the grooves 57 and the multi-lumen tube 1 with which the outer shape of the cross section is a perfect circle can be obtained.

As described above, even with the extrusion molding apparatus 200 according to the present embodiment, the outer shape of the multi-lumen tube 1 before curing can be molded to a circular cylindrical shape using the outer surface molding apparatus 50 and a multi-lumen tube with which the outer shape of the cross section is close to a perfect circle can be produced. With the present embodiment, since the first belt 51 and the second belt 52 are used in the outer surface molding apparatus 50, positioning of the first belt 51 and the second belt 52 is unnecessary, unlike in a case of using non-continuous mold blocks. Also, since there are no joints in the grooves 57 of the first belt 51 and the second belt 52, the outer surface of the multi-lumen tube 1 can be made smoother.

Modification Examples

Although with each of the embodiments described above, an example where a resin supplying portion is constituted of a single extruder 11, the resin supplying portion may instead be constituted of a first extruder that extrudes a first resin, a second extruder that extrudes a second resin differing in hardness from the first resin, and a valve mechanism that controls the supply of the resins to a die. The valve mechanism may be capable of switching between a first state in which the first resin extruded from the first extruder is supplied to the die and the second resin extruded from the second extruder is not supplied to the die and a second state in which the first resin extruded from the first extruder is not supplied to the die and the second resin extruded from the second extruder is supplied to the die. As such a valve mechanism, for example, an arrangement described in International Publication No. WO 2020/262480 can be adopted. Or, the valve mechanism may supply a mixed resin of the first resin extruded from the first extruder and the second resin extruded from the second extruder to the die while changing a mixing ratio of the first resin and the second resin. As such a valve mechanism, for example, an arrangement described in International Publication No. WO 2019/177018 can be adopted. Operation of the valve mechanism can be controlled by the controller 16 described above. By adopting the resin supplying portion that includes the two extruders and the valve mechanism, it is made possible to mold a multi-lumen tube with which one end side and another end side differ in hardness.

The present invention can be used in a multi-lumen tube production apparatus.

Although the present invention has been described in detail above, the above description merely provides examples of the present invention in all respects and is not intended to limit the scope thereof. It is needless to say that various improvements and modifications can made without departing from the scope of the present invention.

What is claimed is:

1. An extrusion molding apparatus for a multi-lumen tube having two or more conduits, the multi-lumen tube extrusion molding apparatus comprising:

a resin supplying portion that extrudes a molten resin;

a die that has an extrusion port at a lower end portion and molds the multi-lumen tube as the resin supplied from the resin supplying portion is extruded vertically downward;

an outer surface molding apparatus that molds an outer surface of the multi-lumen tube extruded from the die;

a gas supplying apparatus; and a depressurizing apparatus, wherein
the die includes
  an inner die,
  two or more conduit molding members of tubular
    shapes that are provided in correspondence with the
    respective conduits of the multi-lumen tube and with
    each of which a front end portion projects from a
    lower end portion of the inner die and a remaining
    portion is positioned in an interior of the inner die
    and each having a penetrating hole and having, at the
    front end portion, a portion of outer shape corre-
    sponding to a cross-sectional shape of the corre-
    sponding conduit, and
  an outer die of tubular shape that surrounds the inner
    die and the portions projecting from the lower end
    portion of the inner die and forms a resin flow
    passage between its inner surface and an outer sur-
    face of the inner die,
the outer surface molding apparatus includes
  a plurality of first mold blocks each having a flat
    surface with which an outer shape is a rectangular
    shape, a groove of rectilinear shape that is provided
    on the flat surface and with which a cross section in
    a direction orthogonal to the flat surface is a semi-
    circular shape, and a slit or a pore that penetrates
    through the groove,
  second mold blocks of the same shape and same
    number as the first mold blocks; and
  a driving mechanism that pairs and circulates the first
    mold blocks and the second mold blocks,
the driving mechanism
  causes, in a molding zone provided vertically below the
    die, the flat surfaces of each paired first mold block
    and second mold block to be in surface contact with
    each other such that the grooves thereof overlap
    mutually, a molding space with which a lateral cross
    section is of a perfect circular shape and a center of
    the lateral cross section coincides substantially with
    a central axis of the die to be formed between the
    mutually overlapped grooves, and a successive plu-
    rality of pairs of the first mold block and the second
    mold block to undergo rectilinear movement verti-
    cally downward along the central axis of the die and
  causes, outside the molding zone, each paired first mold
    block and second mold block to separate from each
    other, and
in a state in which the resin is supplied from the resin
  supplying portion to the die,
  a gas is supplied from the gas supplying apparatus to
    each of the conduit molding members, the supplied
    gas is injected from front ends of the penetrating
    holes,
  the driving mechanism causes, in a state in which the
    multi-lumen tube extruded from the die is contained
    in the molding space of each of the successive
    plurality of pairs of the first mold block and the
    second mold block, the first mold blocks and the
    second mold blocks to move vertically downward in
    accordance with the extrusion of the multi-lumen
    tube, and
  the molding space is depressurized by the depressur-
    izing apparatus to put the outer surface of the multi-
    lumen tube contained in the molding space in close
    contact with inner surfaces of the grooves.
  2. An extrusion molding apparatus for a multi-lumen tube
having two or more conduits, the multi-lumen tube extrusion
molding apparatus comprising:

a resin supplying portion that extrudes a molten resin;
a die that has an extrusion port at a lower end portion and
  molds the multi-lumen tube as the resin supplied from
  the resin supplying portion is extruded vertically down-
  ward;
an outer surface molding apparatus that molds an outer
  surface of the multi-lumen tube extruded from the die;
a gas supplying apparatus; and
a depressurizing apparatus, wherein
the die includes
  an inner die,
  two or more conduit molding members of tubular
    shapes that are provided in correspondence with the
    respective conduits of the multi-lumen tube and with
    each of which a front end portion projects from a
    lower end portion of the inner die and a remaining
    portion is positioned in an interior of the inner die
    and each having a penetrating hole and having, at the
    front end portion, a portion of outer shape corre-
    sponding to a cross-sectional shape of the corre-
    sponding conduit; and
  an outer die of tubular shape that surrounds the inner
    die and the portions projecting from the lower end
    portion of the inner die and forms a resin flow
    passage between its inner surface and an outer sur-
    face of the inner die,
the outer surface molding apparatus includes
  a first belt formed of a material with flexibility and
    having a flat surface, a groove of rectilinear shape
    that is provided on the flat surface and with which a
    cross section in a direction orthogonal to the flat
    surface is a semicircular shape, and a slit or a pore
    that penetrates through the groove,
  a second bell formed of the same material as the first
    belt and having the same shape as the first belt, and
  a driving mechanism that circulates the first belt and the
    second belt,
the driving mechanism
  causes, in a molding zone provided vertically below the
    die, the flat surfaces of the first belt and second belt
    to be in surface contact with each other such that the
    grooves thereof overlap mutually, a molding space
    with which a lateral cross section is of a perfect
    circular shape and a center of the lateral cross section
    coincides substantially with a central axis of the die
    to be formed between the mutually overlapped
    grooves, and the first belt and the second belt to
    undergo rectilinear movement vertically downward
    along the central axis of the die and
  causes, outside the molding zone, the first belt and the
    second belt to separate from each other, and
in a state in which the resin is supplied from the resin
  supplying portion to the die,
  a gas is supplied from the gas supplying apparatus to
    each of the conduit molding members, the supplied
    gas is injected from front ends of the penetrating
    holes,
  the driving mechanism causes, in a state in which the
    multi-lumen tube extruded from the die is contained
    in the molding space formed by the first belt and the
    second belt, the first belt and the second belt to move
    vertically downward in accordance with the extru-
    sion of the multi-lumen tube, and
  the molding space is depressurized by the depressur-
    izing apparatus to put the outer surface of the multi-
    lumen tube contained in the molding space in close
    contact with inner surfaces of the grooves.

3. The multi-lumen tube extrusion molding apparatus according to claim 1, further comprising: an elevating/lowering mechanism that elevates and lowers the outer surface molding apparatus in a vertical direction.

4. The multi-lumen tube extrusion molding apparatus according to claim 1, wherein respective upper end positions of the conduit molding members differ.

5. The multi-lumen tube extrusion molding apparatus according to claim 1, wherein at least one of the conduit molding members includes a first member of tubular shape that includes the front end portion and a second member of tubular shape and an upper end of the first member is detachably connected to a lower end of the second member.

6. The multi-lumen tube extrusion molding apparatus according to claim 1, wherein an inner diameter of the outer die is not more than 10 mm.

7. The multi-lumen tube extrusion molding apparatus according to claim 1, wherein the multi-lumen tube is a medical tube.

8. The multi-lumen tube extrusion molding apparatus according to claim 1, wherein the resin supplying portion includes a single extruder that extrudes the molten resin.

9. The multi-lumen tube extrusion molding apparatus according to claim 1, wherein the resin supplying portion includes:

a first extruder that extrudes a first resin;

a second extruder that extrudes a second resin differing in hardness from the first resin; and a valve mechanism that is capable of switching between a first state in which the first resin extruded from the first extruder is supplied to the die and the second resin extruded from the second extruder is not supplied to the die and a second state in which the first resin extruded from the first extruder is not supplied to the die and the second resin extruded from the second extruder is supplied to the die.

10. The multi-lumen tube extrusion molding apparatus according to claim 1, wherein the resin supplying portion includes:

a first extruder that extrudes a first resin;

a second extruder that extrudes a second resin differing in hardness from the first resin; and a valve mechanism that supplies a mixed resin of the first resin extruded from the first extruder and the second resin extruded from the second extruder to the die while changing a mixing ratio of the first resin and the second resin.

11. The multi-lumen tube extrusion molding apparatus according to claim 2, further comprising: an elevating/lowering mechanism that elevates and lowers the outer surface molding apparatus in a vertical direction.

12. The multi-lumen tube extrusion molding apparatus according to claim 2, wherein respective upper end positions of the conduit molding members differ.

13. The multi-lumen tube extrusion molding apparatus according to claim 2, wherein at least one of the conduit molding members includes a first member of tubular shape that includes the front end portion and a second member of tubular shape and an upper end of the first member is detachably connected to a lower end of the second member.

14. The multi-lumen tube extrusion molding apparatus according to claim 2, wherein an inner diameter of the outer die is not more than 10 mm.

15. The multi-lumen tube extrusion molding apparatus according to claim 2, wherein the multi-lumen tube is a medical tube.

16. The multi-lumen tube extrusion molding apparatus according to claim 2, wherein the resin supplying portion includes a single extruder that extrudes the molten resin.

17. The multi-lumen tube extrusion molding apparatus according to claim 2, wherein the resin supplying portion includes:

a first extruder that extrudes a first resin;

a second extruder that extrudes a second resin differing in hardness from the first resin; and a valve mechanism that is capable of switching between a first state in which the first resin extruded from the first extruder is supplied to the die and the second resin extruded from the second extruder is not supplied to the die and a second state in which the first resin extruded from the first extruder is not supplied to the die and the second resin extruded from the second extruder is supplied to the die.

18. The multi-lumen tube extrusion molding apparatus according to claim 2, wherein the resin supplying portion includes:

a first extruder that extrudes a first resin;

a second extruder that extrudes a second resin differing in hardness from the first resin; and a valve mechanism that supplies a mixed resin of the first resin extruded from the first extruder and the second resin extruded from the second extruder to the die while changing a mixing ratio of the first resin and the second resin.

* * * * *